United States Patent [19]

Yamazoe et al.

[11] Patent Number: 4,718,991
[45] Date of Patent: Jan. 12, 1988

[54] PROTON CONDUCTOR GAS SENSOR AND METHOD OF DETECTING GAS USING PROTON CONDUCTOR GAS SENSOR

[75] Inventors: Noboru Yamazoe; Norio Miura, both of Hukuoka, Japan

[73] Assignee: Figaro Engineering Inc., Japan

[21] Appl. No.: 5,245

[22] Filed: Jan. 20, 1987

[30] Foreign Application Priority Data

Jan. 27, 1986 [JP] Japan ................ 61-15222

[51] Int. Cl.$^4$ ............................................. G01N 27/56
[52] U.S. Cl. ..................... 204/1 T; 204/410;
204/412; 204/421; 204/424; 204/426; 324/71.1;
338/34; 422/98; 436/144
[58] Field of Search ............... 204/412, 410, 421, 424,
204/425, 426, 427, 428, 429, 1 T, 1 K, 1 N, 1 F;
338/34; 422/98; 436/144; 324/71.1, 61 R

[56] References Cited

U.S. PATENT DOCUMENTS

| | | | |
|---|---|---|---|
| 3,410,780 | 11/1968 | Holden | 204/426 X |
| 3,479,257 | 11/1969 | Shaver | 436/144 |
| 3,727,058 | 4/1973 | Schrey | 204/424 X |
| 4,030,340 | 6/1977 | Chang | 73/23 |
| 4,324,760 | 4/1982 | Harris | 422/98 |
| 4,324,761 | 4/1982 | Harris | 422/98 |
| 4,513,069 | 4/1985 | Kreuer et al. | 429/192 |
| 4,661,211 | 4/1987 | Petty-Weeks | 204/1 T |
| 4,664,757 | 5/1987 | Zupancic et al. | 204/1 T |

FOREIGN PATENT DOCUMENTS

| | | | |
|---|---|---|---|
| 50458 | 3/1983 | Japan | 204/421 |
| 7358 | 1/1985 | Japan | 324/71.1 |

OTHER PUBLICATIONS

N. Miura et al., Proceedings of the International Meeting on Chemical Sensor, Fukuoka, Japan, pp. 233-238, Sep. 19-22, (1983).

*Primary Examiner*—G. L. Kaplan
*Attorney, Agent, or Firm*—Kane, Dalsimer, Kane, Sullivan & Kurucz

[57] ABSTRACT

A proton conductor gas sensor operable at room temperature for detecting hydrogen or carbon monoxide, and a gas detecting method using the sensor. A pair of electrodes connected to a proton conductor are short-circuited to cause protons to travel through the conductor utilizing the difference in activity between the electrodes or the difference in gas permeability between the electrode and an atmosphere containing the gas to be detected. The potential difference produced in the interior of the conductor by the travel of the protons is obtained as the output of the sensor. This output is in proportion to the concentration of the gas and low in humidity dependence.

10 Claims, 10 Drawing Figures

PROTON CONDUCTOR GAS SENSOR AND METHOD OF DETECTING GAS USING PROTON CONDUCTOR GAS SENSOR

BACKGROUND OF THE INVENTION

1. Field of the Invention

The present invention relates to proton gas sensors and to a method of detecting a gas using the proton gas sensor. The gases to be detected according to the present invention are chiefly hydrogen and carbon monoxide and include other gases such as silanes, arsines, sulfur dioxide and nitrogen oxides. More particularly, the invention relates to the detection of these gases in oxygen-containing atmospheres such as air.

2. Prior Art

Kiyoyama et al. disclose a proton conductor gas sensor in unexamined Japanese patent publication SHO No. 60-7358 or in "Proceedings of the International Meeting on Chemical Sensors," pp. 233–238, Kodansha, 1983 corresponding to the publication. The basic feature of this sensor is that it is operable at room temperature. Further various proton conductors are already known for use in such sensors. For example, the above publication mentions proton conductors such as zirconium phosphate ($Zr(HPO_4)_2 \cdot nH_2O$), dodecamolybdophosphoric acid ($H_3Mo_{12}PO_{40} \cdot 30H_2O$), antimonic acid ($Sb_2O_5 \cdot nH_2O$, wherein n is usually about 2) and Nafion (trademark of E. I. du Pont de Nemours for perfluorocarbon sulfonate). In addition, Iwahara et al. have made a report on the proton conductivity of $SrCeO_3$ wherein the Ce element is partly substituted with Y, Yb or like element ("Proceedings of the International Meeting on Chemical Sensors," pp. 227–232, Kodansha, 1983).

The Kiyoyama et al. sensor disclosed in unexamined Japanese patent publication SHO No. 60-7358 comprises a proton conductor, and an active electrode of platinum or the like and an inactive electrode of silver, gold, graphite or the like which are connected to the conductor. The platinum electrode decomposes a gas such as hydrogen by an electrode reaction to produce protons. However, the inactive electrode of silver or the like exhibits no activity to decompose hydrogen, with the result that an electromotive force occurs between the two electrodes. Thus, hydrogen or like gas is detected in the absence of any reference gas. Kiyoyama et al. further show that not only hydrogen but also carbon monoxide is also detectable with proton conductors.

With the Kiyoyama et al. sensor, the electromotive force varies in proportion to the logarithm of the gas concentration. In detecting hydrogen at room temperature with the sensor, a tenfold increase in the gas concentration results in a variation of 140 mv in the electromotive force. Further with this sensor, the electromotive force is not zero even in clean air; the sensor exhibits an electromotive force of 400 to 500 mv in clean air. The electromotive force occurring in clean air is thought attributable to an interfacial potential resulting from the difference between the two electrodes.

We have conducted research to obtain an output in proportion to the gas concentration and to obtain outputs with zero-point compensation, i.e., outputs relative to the output in clean air which is corrected to zero, and found that if two electrodes are short-circuited, the short-circuit current measured provides an output which is zero in clean air on proportion to the gas concentration. The current results from the travel of protons from an active electrode to an inactive electrode. On the other hand, the aforementioned electromotive force is not due to the travel of protons but to a hybrid potential at the active electrode. The electromotive force is measured with the external impedance to be connected between the two electrodes made almost infinitely great. In the case of the short-circuit current, the two electrodes are short-circuited externally to permit protons to travel in the interior of the conductor and obtain the resulting current.

Nevertheless, the short-circuit current was found sensitive to humidity, especially to relative humidity (FIG. 6), whereas the electromotive force was low in humidity dependence.

SUMMARY OF THE INVENTION

The object of the present invention is
(1) to obtain an output in proportion to the the gas concentration, and
(2) to diminish the humidity dependence of the output.

According to the present invention, three kinds of electrodes, i.e. an ionization electrode, reference electrode and detection electrodes, are connected to a proton conductor to provide a gas sensor. With the ionization electrode and the reference electrode short-circuited, the potential across the detection electrodes is measured to detect the gas concerned.

The ionization electrode decomposes hydrogen or like gas in the ambient atmosphere to give protons to the conductor. The reference electrode receives the protons from the conductor, causing them to react with the oxygen in the atmosphere to release water. In the case of hydrogen, the electrode reaction primarily takes place as follows.

In the case of carbon monoxide, the reaction chiefly occurs as follows.

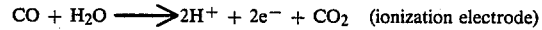

The ionization electrode and the reference electrode are short-circuited on the sensor itself or on a circuit attached thereto. These electrodes may be connected together via a low-impedance load such as an ammeter. This connection results in substantially the same result as the short-circuiting, so that the short-circuiting includes this connection. The ionization electrode and the reference electrode are short-circuited to permit free travel of electrons as required for the electrode reaction. The intermediate load to be connected should be one which is lower than the proton conductor in impedance. Proton conductors generally have an impedance of about 1 to about 50 k$\Omega$. The impedance of the external load should be lower than this level, preferably up to 1/5 of that of the proton conductor.

The resulting current, although proportional to the gas concentration, varies with the humidity. The potential difference produced by the current within the proton conductor (hereinafter referred to as "internal potential difference") is in proportion to the gas concentration and is low in humidity dependence. In the case of hydrogen, for example, the humidity dependence of the internal potential difference is negligible. When the potential difference is detected by the detection electrodes, an output is available which is in proportion to the gas concentration and low in humidity dependence.

The reason why the internal potential difference is low in humidity dependence can be explained as follows. Suppose the internal potential difference is E, the short-circuit current is i and the internal resistance of the proton conductor is R. These values have the relation of $E = i.R$. The humidity increases the current i but decreases the internal resistance R. The internal potential difference E, which is the product of i multiplied by R, is low in humidity dependence.

Preferably, a pair of detection electrodes is used. The voltage across the electrodes affords the internal potential difference. In this case the output in clean air is zero, and outputs are available all with zero-point compensation. However, a single detection electrode may be used to detect the potential difference between the detection electrode and the ionization electrode or the reference electrode.(The latter two electrodes, when short-circuited, are at the same potential level.) In this arrangement, nevertheless, the interfacial potential between the proton conductor and the ionization or reference electrode appears as an output, so that the output in clean air is not zero.

According to the present invention, gases such as hyrogen, arsines and silanes which readily decompose to produce protons can be detected. In the case of these gases, the output is low in humidity dependence. Also detectable are gases, such as carbon monoxide, sulfur dioxide and nitrogen oxides, which produce protons on reacting with water vapor. In this case, however, the electrode reaction on the ionization electrode is in itself dependent on humidity to give an output which is dependent on humidity. In the case of other gases, e.g. ethanol, the output is up to 1/100 of the output for hydrogen. The present sensor is almost insensitive to methane, propane and like gases. The present sensor is equivalent to the sensor of Kiyoyama et al. in humidity dependence. Both are low in the humidity dependence of the sensitivity to hydrogen, while their outputs for carbon monoxide involve humidity dependence due to the electrode reaction.

EMBODIMENTS

Construction of Sensors

Figure 1:
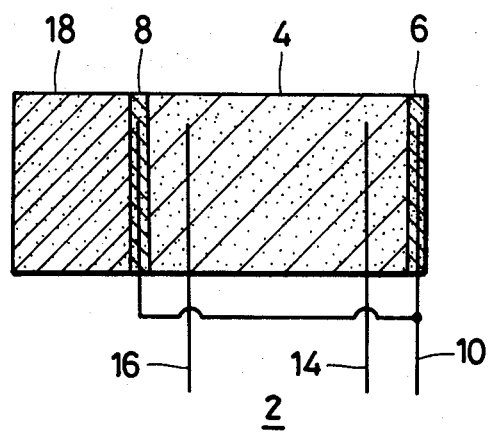
FIG. 1 is a sectional view showing a proton conductor gas sensor embodying the invention.

FIG. 1 shows a proton conductor gas sensor 2 comprising a press-molded proton conductor 4. The term "proton conductor" refers to a substance wherein protons mainly serve as carriers to exhibit electric conductivity. Usable as the proton conductor 4 is any of antimonic acid ($Sb_2O_5.nH_2O$ wherein n is usually about 2), zirconium phosphate ($H_2ZrP_2O_8.H_2O$), dodecamolybdophosphoric acid ($H_3Mo_{12}PO_{40}.nH_2O$ wherein n is usually about 30), uranyl hydrogenphosphate tetrahydrate ($HUO_2PO_4.4H_2O$), Nafion (trademark of E. I. du Pont de Nemours for perfluorocarbon sulfonate), etc. These substances contain as a constituent element hydrogen which is present in the form of a proton. Also usable is $SrCeO_3$ wherein about 5% of the Ce element is replaced by Y, Yb or like element. In this case, the water vapor diffused through the interior of cystals decomposes to release protons to exhibit conductivity. These protons serving as carriers are mobile in the interior of crystals to exhibit conductivity. The mobility of protons increases with the water content of the crystal, so that the internal resistance decreases with humidity.

These substances are used singly, or two of them are used in admixture. An organic binder, inorganic insulating material, etc. are admixed with the substance or the mixture. The following description is given of the use of antimonic acid as admixed with 20 wt. % of polyethylene tetrafluoride serving as a binder, chiefly for the detection of hydrogen and carbon monoxide. Use of other proton conductors was found to achieve comparable results. The thickness of the conductor 4 between an ionization electrode 6 and a reference electrode 8 is about 2 mm. Preparation of antimonic acid will be described later.

The ionization electrode 6 is in the form of a film of platinum powder adhered to the proton conductor 4. The ionization electrode 6 decomposes hydrogen or like gas in the atmosphere through an electrode reaction to produce protons. Examples of preferred materials for the ionization electrode 6 are, beside platinum, rhodium, iridium (present chiefly in the form of a metal), ruthenium, palladium, rhenium (present chiefly in the form of a metallic oxide), etc. Also usable for the ionization electrode 6 is a perovskite, such as a mixture of $LaNiO_3$ and platinum. A platinum wire may singly be used as the electrode 6.

The reference electrode 8 is similarly in the form of a film of platinum powder. The reference electrode 8 accepts protons from the conductor and causes them to react with the oxygen in the atmosphere to produce water. Any desired electrode is usable as the reference electrode 8 insofar as it is capable of effecting the reaction of protons with oxygen. Examples of desired materials for the electrode 8 are highly reactive platinum, rhodium, iridium, ruthenium, palladium, conductive perovskite, etc. Also usable are silver, gold, graphite, stannic oxide and the like.

The ionization electrode 6 and the reference electrode 8 are short-circuited by a lead wire 10. Indicated at 14 and 16 are paired detection electrodes, each of which is a silver wire implanted in the conductor 4. To avoid an electrode reaction on the detection electrodes, it is desirable that these electrodes be made of a material which is low in catalytic activity. Desirable materials other than silver are gold, stannic oxide, indium oxide, etc.

Indicated at 18 is a shield for restricting passage of gas toward the reference electrode 8. A film of antimonic acid, 0.6 mm in thickness, is used as the shield 18. Owing to the restriction of gas permeability by the shield 18 and to the reaction between hydrogen and oxygen on the reference electrode 8, a hydrogen concentration difference occurs between the reference electrode 8 and the ionization electrode 6. The concentration difference permits protons to travel between the two electrodes, producing a short-circuit current through the lead wire 10.

Figure 2:
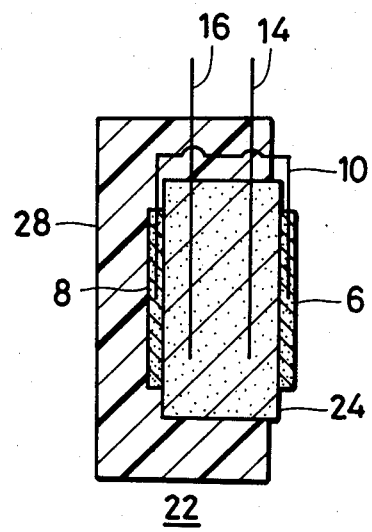
FIG. 2 is a sectional view showing another proton conductor gas sensor embodying the invention.

FIG. 2 shows another gas sensor 22. A gas-impermeable shield 28 is made of a gas-tight epoxy resin. Oxygen and water are allowed to diffuse through antimonic acid 24. In this case, the resistance of the antimonic acid 24 to permeation of gas results in a low hydrogen concentration at the reference electrode 8. Nevertheless, the ambient atmosphere usually contains a large quantity of oxygen, so that oxygen is present on the reference electrode 8 in such an amount as to react with the protons reaching the elctrode 8 to produce water. The sensor 22 is equivalent to the sensor 2 of FIG. 1 in characteristics.

Figure 3:
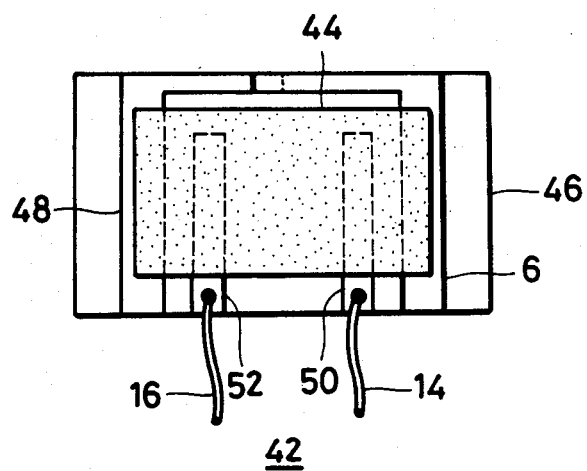
FIG. 3 is a front view showing another proton conductor gas sensor embodying the invention.

FIG. 3 shows a gas sensor 42 which is simplified in configuration and made amenable to mass production. Indicated at 44 is a film of antimonic acid, at 46 an insulation substrate, and at 48 a reference electrode of silver film which is connected to an ionization electrode 6 for shorting. Detection electrodes 50 and 52 are each made of silver film. At the silver electrode 48, the reaction of $H_2 \rightarrow 2H^+ + 2e^-$ does not occur, but the reaction of $2H^+ + 2e^- + \frac{1}{2}O_2 \rightarrow H_2O$ takes place. Accordingly, even if the reference electrode 48 is exposed to the atmosphere, a current flows between the electrode 48 and the ionization electrode 6. The detection electrodes 50 and 52 detect the internal potential difference of the conductor 44 due to this current. This sensor 42 is similar to the sensor 2 in characteristics, while the short-circuit current and the internal potential difference were up to $\frac{1}{2}$ of the corresponding values of the sensor 2.

With this sensor, the four electrodes 6, 48, 50 and 52 can be formed as by printing, and the electrodes 6 and 48 can be short-circuited merely by superposing a film by printing. Similarly, the proton conductor 44 can also be formed by printing. Accordingly, this feature almost completely obviates the difficulty to be otherwise encountered in providing the four electrodes. The advantage of ease of fabrication more than offsets the drawback that the output is up to $\frac{1}{2}$ of that of the sensor 2.

Figure 5:
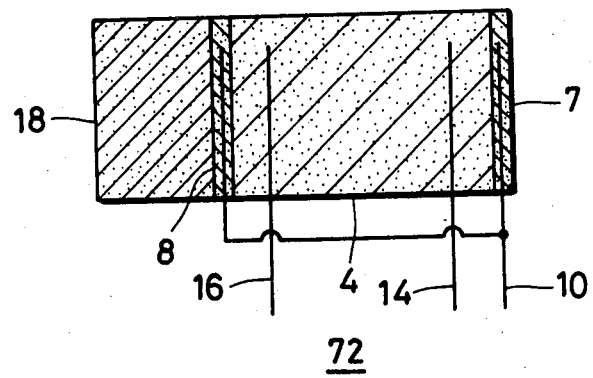
FIG. 5 is a sectional view showing another proton conductor gas sensor embodying the invention.

The technique embodying the sensors of FIGS. 1 and 2 and another sensor of FIG. 5 is also applicable to the sensor of FIG. 3. The silver electrode 48 may alternatively be an electrode of low activity, such as one made of stannic oxide, indium oxide or the like. Further the gas permeability restricting shield of FIG. 1 or 2 may serve as a reference electrode. In this case, the electrodes 48 and 6 are a single film of platinum or the like. Preferably, the detection electrodes 50 and 52 are made of silver, gold, stannic oxide or indium oxide. The electrodes need not always be formed by printing but may be provided, for example, by vacuum evaporation or sputtering. A flat plate is used as the substrate 46 to render the electrodes easily printable. The substrate may be an insulation pipe or otherwise shaped. The up-down relation between the proton conductor 44 and the electrodes 6, 50 may be reversed.

Preparation of Antimonic Acid

To antimony trioxide ($Sb_2O_3$) was added an aqueous solution of hydrogen peroxide in 15 times the amount equivelent to the trioxide, and the mixture was heated to 60° C. with stirring. About 30 minutes after the heating, antimony started to oxidize from trivalent to pentavalent, and the solution exhibited a pale yellow fluorescence. The solution was maintained at 60° C. until the fluorescence disappeared and thereafter at 80° to 100° C. for 30 hours. During this stage, antimonic acid separated out as a white precipitate. The precipitate was filtered off, centrifuged with addition of water and dried to obtain a specimen of antimonic acid.

The antimonic acid had the composition of $Sb_2O_5 \cdot 2H_2O$ and remained free of decomposition below 500° C. Accordingly, the sensors 2, 22, 42, etc, embodying the invention are usable at a temperature of up to 500° C., preferably up to 300° C.

Attached Circuit

Figure 4:
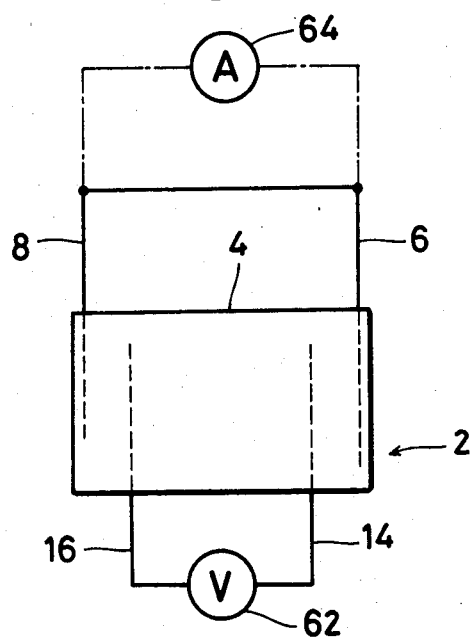
FIG. 4 is a diagram showing a circuit attached to the present sensor.

FIG. 4 shows an example of circuit attached to the present sensor. A voltmeter 62 is connected between the detection electrodes 14 and 16 to detect the internal potential difference of the proton conductor 4. The ionization electrode 6 and the reference electrode 8 are short-circuited. Actual measurement was done with an ammeter 64 connected between the ionization electrode 6 and the reference electrode 8 as separated from each other. The ratio between the signal from the ammeter 64 and the signal from the voltmeter 62 is dependent on relative humidity. The relative humidity is therefore detectable from this ratio.

Carbon Monoxide Sensor

In the foregoing embodiments, the following reaction (A) occurs in preference to the reaction (B) given below, so that the relative sensitivity to carbon monoxide is low.

$$H_2 \rightarrow 2H^+ + 2e^- \tag{A}$$

$$CO + H_2O \rightarrow CO_2 + 2H^- + 2e^- \tag{B}$$

The sensitivity to carbon monoxide relative to the sensitivity to hydrogen can be improved by using an electrode which selectively adsorbs carbon monoxide to effect the reaction (B), or by using an electrode which selectively removes hydrogen by combustion.

FIG. 5 shows a sensor 72 so constructed. The ionization electrode 7 of this sensor is made of a mixture of 80 wt. % of platinum powder and 20 wt. % of tetraphenylporphyrin coordinated with cobalt atom (Co-TPP). Porphyrins remove hydrogen by combustion and promote adsorption of carbon monoxide.

Porphyrins are organic compounds known as active centers for hemoglobin and other enzymes and readily combine with metals to form coordination compounds. The porphyrin to be used is not limited to tetraphenylporphyin, but any porphyrin such as octaethylporphyrin is usable. The Co element may be replaced by some other transition metal element such as Fe, Ni, Mn, Cu, Zn or the like. The platinum for the electrode may be replaced by some other highly active electrode material such as rhodium, iridium, ruthenium, palladium, rhenium or the like. The porphyrin may be replaced by some other compound analogous thereto, such as phthalocyanine, choline or the like. The present embodiment is characterized in that the electrode 7 has incorporated therein a metalloporphyrin, and the structure shown in FIG. 2 or 3 may alternatively be used. The mixture for forming the electrode is composed preferably of 90 to 40 wt. % of a noble metal such as platinum and 10 to 60 wt. % of a porphyrin compound, more preferably 90 to 60 wt. % of a noble metal and 10 to 40 wt. % of a porphyrin compound. With a lesser amount of the porphyrin present, the electrode fails to adsorb carbon monoxide with sufficient selectivity, whereas larger quantities result in a reduced gas detection output. The catalytic activity of porphyrins is known (see, for example, The Catalyst, Vol. 26, No. 6, p. 443 1984).

Characteristics of Sensor

The characteristics of the sensor 2 of FIG. 1 will be described below unless otherwise stated, while the sensors of FIGS. 2 and 3 are comparable to the sensor 2 in characteristics. The atmosphere is air.

Figure 6:
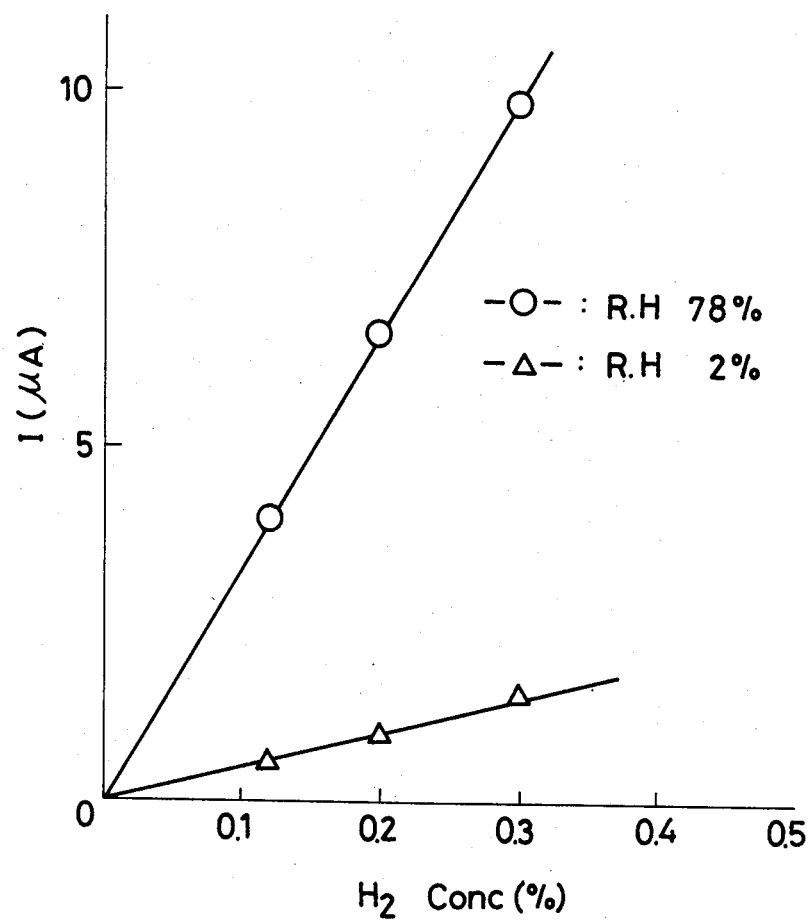
FIG. 6 is a characteristics diagram showing the humidity dependence of the short-circuit current through the embodiment of FIG. 1.

FIG. 6 shows the relation betwen the hydrogen concentration and the short-circuit current between the electrodes 6, 8 at room temperature (27° C.). The output is in proportion to the hydrogen concentration but varies with humidity.

The following becomes apparent as to the short-circuit current. First, the hydrogen concentration at the reference electrode 8 is low because this electrode has the ability to oxidize hydrogen to water even at room temperature and further because the gas permeability is restricted by the shield 18. However, the ambient atmosphere contains a large amount of oxygen, and oxygen is present at the electrode 8 in such an amount that the protons delivered from the conductor 4 can be converted to water. At the ionization electrode 6, the following reaction occurs to dissociate the hydrogen in the atmosphere into protons and electrons.

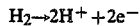

The dissociated protons move through the conductor 4 and reach the reference electrode 8. With a load of low impedance connected between the ionization electrode 6 and the reference electrode 8, the electrons travel through the lead wire 10 to the reference electrode 8, where the following reaction takes place.

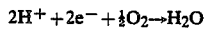

The flow of electrons from the ionization electrode 6 to the reference electrode 8 is a short-circuit current. The short-circuit current has a value approximately in accordance with the reaction velocity of the protons at the reference electrode 8 or with the velocity of dissociation of hydrogen to protons at the ionization electrode 6. When the ionization electrode 6 is insulated from the reference electrode 8 to obtain an electromotive force, the above reaction at the reference electrode 8 will not occur since no electrons are supplied, consequently producing no internal potential difference.

Next, the mobility of protons in the conductor 4 is dependent on the water content of the conductor. Accordingly, the mobility of protons and the internal resistance of the conductor 4 are dependent on humidity, and the short-circuit current varies with humidity.

Figure 7:
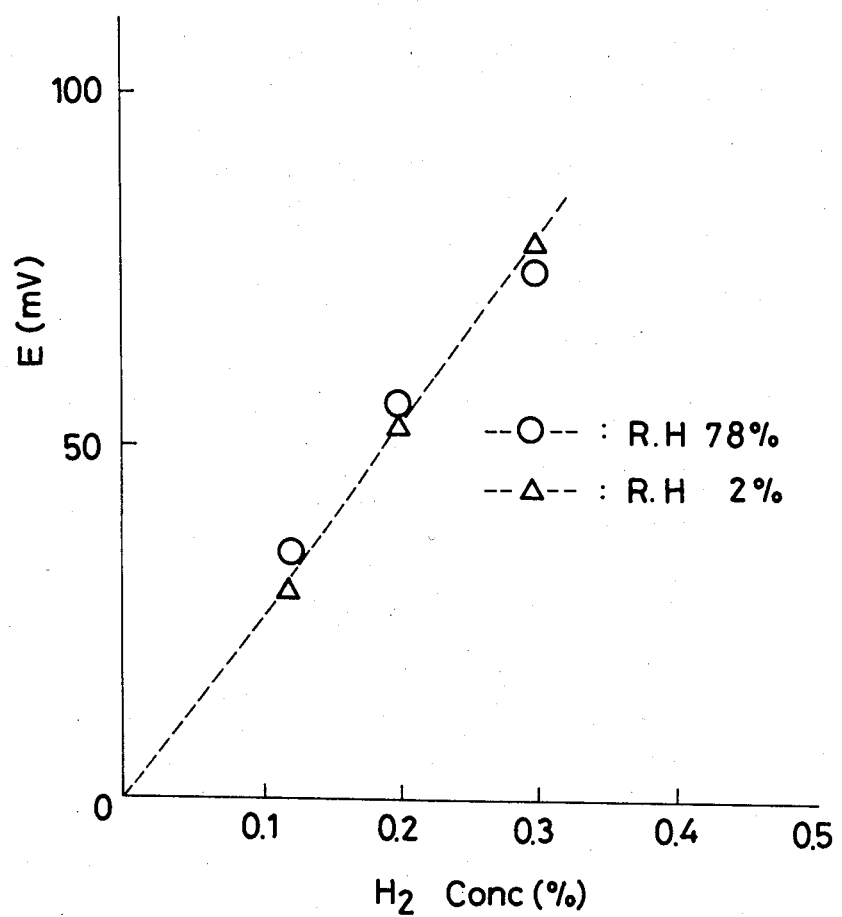
FIGS. 7 to 9 are characteristics diagrams of the embodiment of FIG. 1, FIG. 7 being a characteristics diagram showing the humidity dependence of the internal potential difference, FIG. 8 being a characteristics diagram showing the response of the internal potential difference to changes of atmosphere, and FIG. 9 being a characteristics diagram showing the internal potential difference with lapse of time in the presence of 1.3% hydrogen.

On the other hand, the potential difference between the electrodes 14 and 16 is in proportion to the hydrogen concentration and is almost unaffected by humidity (FIG. 7). Table 1 shows the potential difference between the electrodes 14 and 16 in the presence of 0.2 vol. % of hydrogen at room temperature.

TABLE 1

| Humidity dependence of output (hydrogen) | | | | |
|---|---|---|---|---|
| R.H. (%) | 2 | 30 | 50 | 78 |
| Output (mV) | 51 | 52 | 54 | 56 |

The potential difference is determined by the product of the current through the conductor by the internal resistance of the conductor. The current increases with humidity but the resistance decreases with humidity. The influence of humidity on the potential difference, which is the above product, is small.

Figure 8:
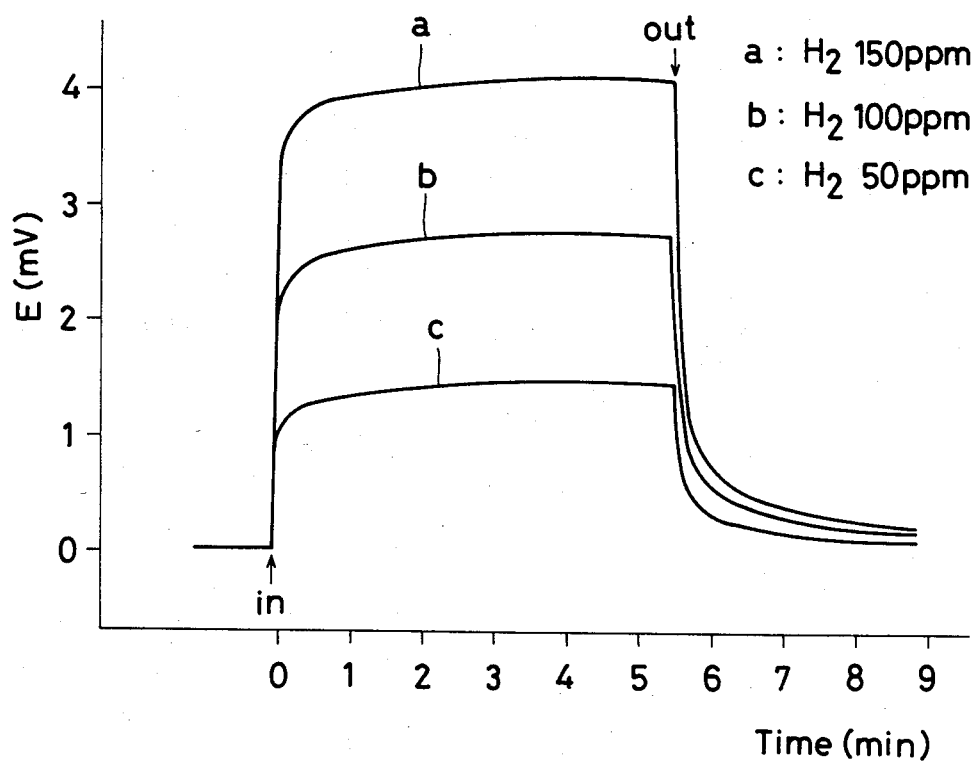
Figure 9:
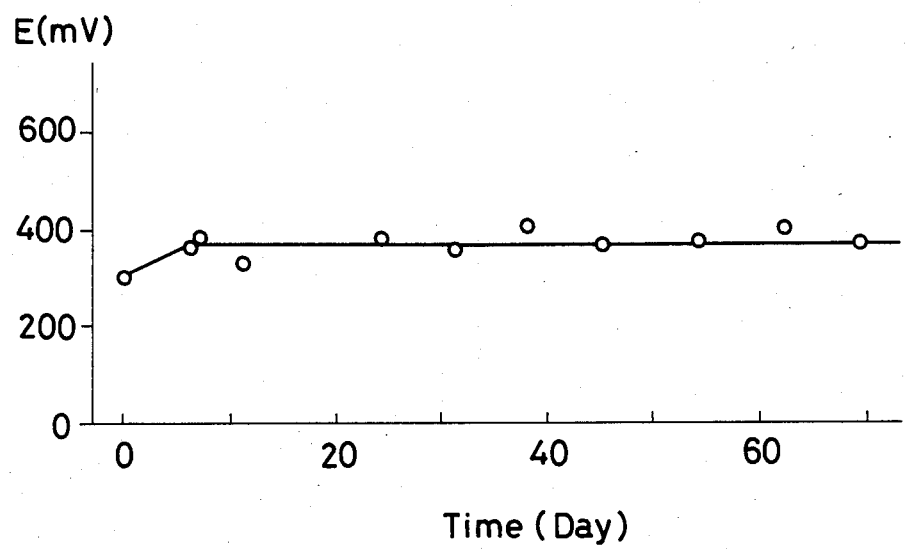

FIG. 8 shows the characteristics of response to hydrogen at different concentrations at room temperature. The internal potential difference is in proportion to the hydrogen concentration and is nearly zero in clean air. FIG. 9 shows the internal potential characteristics with time as determined in the presence of 1.3% of hydrogen at room temperature during 70 days. The output remains almost stable. Although the sensor is used at room temperature and further although the output is dependent on electrode activity, the sensor is operable substantially free of the possible instability.

The problem to be encountered in detecting carbon monoxide is how efficiently the following reaction can be effected at the ionization electrode 6.

$$CO + H_2O \rightarrow 2H^+ + CO_2 + 2e^- \tag{B}$$

To enable the reaction (B) to proceed preferentially, a mixture of platinum and cobalt-coordinated porphyrin (Co-TPP) is used to provide the sensor 72 of FIG. 5. The porphyrin selectively removes hydrogen by combustion and promotes the electrode reaction of carbon monoxide. Table 2 shows variations in the output in response to hydrogen and to carbon monoxide resulting from the presence of the porphyrin. The atmosphere is 72% in R.H. at room temperature. The amount of porphyrin used is in % by weight.

TABLE 2

| Pt (%) | Co—TPP (%) | Potential difference (mV)* | |
|---|---|---|---|
| | | H$_2$ | CO |
| 100 | | 28 | 7 |
| 80 | 20 | 15 | 21 |
| 50 | 50 | 4 | 6 |
| 30 | 70 | 2 | 1 |

Figure 10:
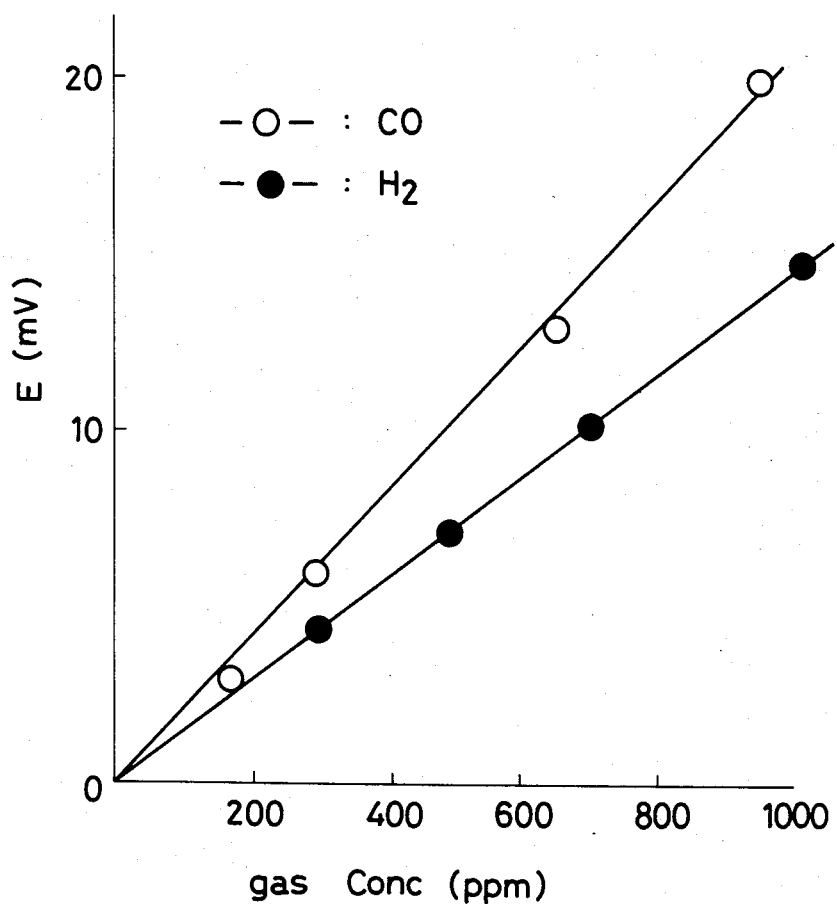
FIG. 10 is a characteristics diagram of the embodiment of FIG. 5.

FIG. 10 shows the output for CO as well as for H$_2$ as determined when the ionization 7 contains 20 wt. % of porphyrin, at room temperature and 72% R.H. The output is in proportion to the gas concentration.

In detecting carbon monoxide, it was impossible to completely obviate humidity dependence since the electrode reaction at the ionization electrode 7 is dependent on humidity. Table 3 shows the short-circuit current and internal potential difference of the sensor of FIG. 5 as determined at 27° C. in the presence of 968 ppm of carbon monoxide. The ionization electrode 6 contains 20 wt. % of porphyrin.

TABLE 3

| | Output for carbon monoxide | | |
|---|---|---|---|
| I (μA) | E (mV) | R (kΩ) | R.H. (%) |
| 0.1 | 6 | 80 | 20 |
| 0.5 | 10 | 30 | 40 |
| 3.1 | 21 | 10 | 72 |

While both the current and the potential difference are dependent on humidity, the potential difference is improved in humidity dependence by an amount corresponding to the variation of internal resistance R.

While the characteristics have been described above as to the sensor wherein antimonic acid is used as the proton conductor, other proton conductors are of course similarly usable. Although the characteristics are described as determined at room temperature, the present sensor is similarly usable at temperatures of up to about 300° C. Further although the atmosphere used for the above description is air, various atmospheres are usable provided that oxygen is contained therein in a larger amount than the gas to be detected. The characteristics of the present sensor for silanes and arsines are similar to those for hydrogen, while the characteristics for sulfur dioxide and nitrogen oxides are similar to those for carbon monoxide.

What is claimed is:

1. A proton conductor gas sensor comprising a proton conductor and a pair of electrodes connected to the conductor, characterized in that one of the electrodes is an ionization electrode for decomposing a gas in an atmosphere by an electrode reaction to produce protons and supplying the protons to the proton conductor, the other electrode being a reference electrode for accepting the protons from the proton conductor, reacting the protons with oxygen in the atmosphere and releasing the resulting water, the sensor having at least one detection electrode for detecting the internal potential difference of the proton conductor produced by the travel of protons between the ionization electrode and the reference electrode when the ionization and reference electrodes are short-circuited.

2. A proton conductor gas sensor as defined in claim 1 wherein the ionization electrode and the reference electrode are short-circuited.

3. A proton conductor gas sensor as defined in claim 1 wherein at least one pair of detection electrodes is provided.

4. A proton conductor gas sensor as defined in claim 3 wherein the detection electrodes are made of at least one material selected from the group consisting of silver, gold, stannic oxide and indium oxide.

5. A proton conductor gas sensor as defined in claim 3 wherein the ionization electrode is made of at least one material selected from the group consisting of the metals of platinum, rhodium, iridium, ruthenium and palladium, and oxides of these metals.

6. A proton conductor gas sensor as defined in claim 5 wherein the reference electrode is shielded from the surroundings by a material for restricting gas permeability.

7. A proton conductor gas sensor as defined in claim 5 wherein the reference electrode is made of at least one material selected from the group consisting of the metals of silver and gold, and oxides of these metals.

8. A proton conductor gas sensor as defined in claim 1 wherein the ionization electrode has incorporated therein at least one member selected from the group consisting of metalloporphyrin, metallophthalocyanine and metallocholine.

9. A proton conductor gas sensor comprising a film of proton conductor supported on an insulation substrate, characterized in that the proton conductor has connected thereto a film of ionization electrode for decomposing a gas in an atmosphere by an electrode reaction and supplying the resulting protons to the proton conductor, a film of reference electrode short-circuited with the ionization electrode for accepting the protons from the conductor, reacting the protons with oxygen in the atmosphere and releasing the resulting water, and a pair of detection electrodes each in the form of a film for detecting the potential difference of the proton conductor produced by the travel of protons from the ionization electrode to the reference electrode.

10. A method of detecting a gas with use of a proton conductor sensor characterized by short-circuiting a pair of electrodes connected to the proton conductor to cause protons to travel through the conductor from one of the electrodes to the other electrode, and detecting the potential difference produced in the conductor by the travel of the protons.

* * * * *